US00PP07815P

United States Patent [19]

McKenzie, deceased et al.

[11] Patent Number: Plant 7,815

[45] Date of Patent: Mar. 3, 1992

[54] APPLE TREE NAMED 'SCIRAY'

[76] Inventors: Don McKenzie, deceased, late of Havelock North; by Joy McKenzie, personal representative, P.O. Box 8345, Havelock North; Allan G. White, R.D. 2, Hastings, all of New Zealand

[21] Appl. No.: 566,641

[22] Filed: Aug. 13, 1990

[51] Int. Cl.[5] ..... A01H 5/00

[52] U.S. Cl. ..... Plt./34

[58] Field of Search ..... Plt./34

[56] References Cited

U.S. PATENT DOCUMENTS

P.P. 2,460 12/1964 Roberts ..... Plt. 34

P.P. 3,637 10/1974 McKenzie ..... Plt. 34

*Primary Examiner*—James R. Feyrer

*Attorney, Agent, or Firm*—Quarles & Brady

[57] ABSTRACT

The new and distinct variety is a selection from seedlings derived from crossing the apple varieties known as "Gala" (U.S. Plant Pat. No. 3,637) and "Splendour" (U.S. Plant Pat. No. 2,460). The fruit of the apple tree of this new variety has an attractive appearance characterized by its striped color pattern. The new variety has been named "Sciray".

1 Drawing Sheet

SUMMARY OF THE INVENTION

The new variety was selected from a population of seedlings derived from crossing the apple varieties "Splendour" (U.S. Plant Pat. No. 2,460) and "Gala" (U.S. Plant Pat. No. 3,637) in 1984. The new variety was distinguishable from the parent varities "Splendour" and "Gala" as well as the varieties Sciros; Sciglo; and Scieur (subject of co-pending applications filed on even date herewith by the same applicants). The features which distinguish the new variety from the aformentioned varieties are:

Gala: Later maturity, fruit size larger, fruit shape rounder, background colour of skin more green.

Splendour: Earlier maturity, fruit shape less flat, striped colour pattern, red-orange colour.

Sciros: Earlier maturity, tree growth habit more vigorous, fruit colour red-orange, striped colour patterns.

Sciglo: Later fruit maturity, larger fruit size, colour red-orange, not such heavy colouring, fruit shape less conical.

Scieur: Fruit taller, less flat, background colour less green, no stem russet, flesh firmer, flavour less acid.

The new variety has been named "Sciray" variety. Asexual propagation by budding shows that the unique combination of characteristics and distinctive colour come true to form and are established and transmitted through succeeding propagations.

BRIEF DESCRIPTION OF THE DRAWINGS

The accompanying drawings show typical specimens of the foliage and fruit of the new variety as depicted in colours as nearly true as is reasonably possible to make the same in a colour illustration of this character.

View A is a side view of an apple of the variety.

View B is a bottom view of an applie of the variety.

View C is a cross sectional view of an apple of the variety.

View D is a top view of an apple of the variety.

Figure 1:
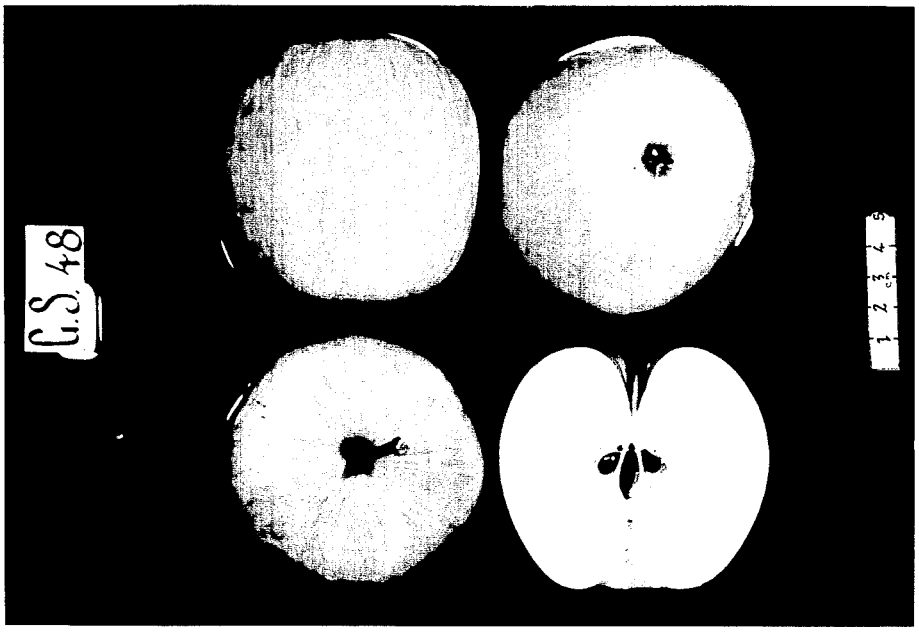
FIG. 1 represents four views of an apple of the new variety. Beginning in the upper right corner and proceeding clockwise.
Figure 2:
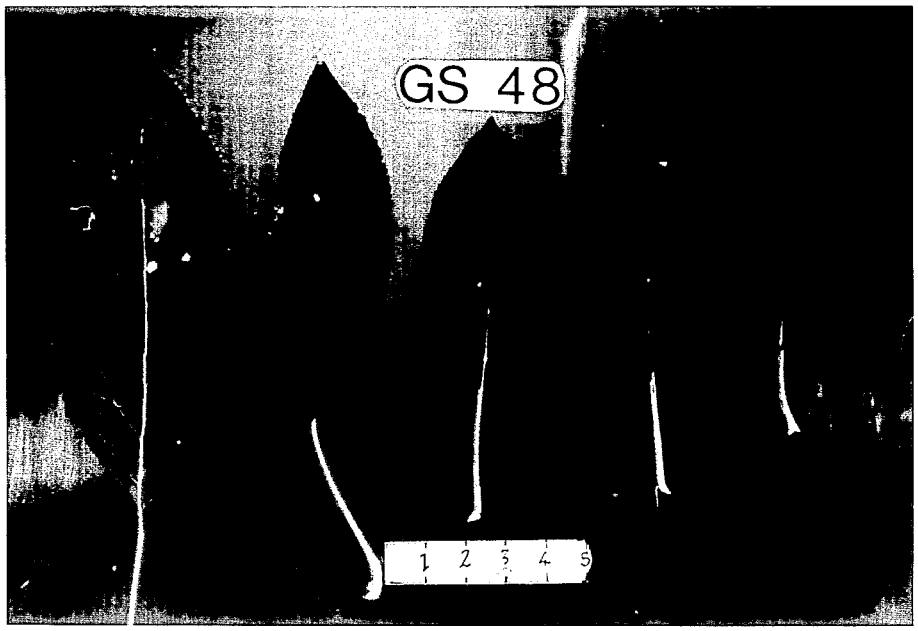

FIG. 2 is a view showing five leaves of the variety.

DETAILED DESCRIPTION OF THE DISCLOSURE

The following is a detailed description of the new variety with color terminology in accordance with The Royal Horticultural Society Colour Chart (R.H.S.C.C.) except where general color terms of ordinary meaning are used as is clear from the context.

The specimens described were grown at Havelock North, New Zealand. The observations were made in the 1989 season on trees which were three years old at the time.

The fruit ripened for eating towards mid-season. Specifically harvest commences about March 10 and ends about March 30 in New Zealand. The blossom commences about September 26 and full bloom occurs about October 5 in New Zealand.

Tree: Medium vigor with annual growth for five year old trees with MM106 rootstock being about 430 mm; upright habit; bearing, on spurs which branch at a rate of 4 per 10 cm. on three year old growth.

Trunk: Moderate smoothness; medium size; the bark is R.H.S.C.C. 166A when new and R.H.S.C.C. 201D when old.

Branches: Thick, moderate smoothness; moderate branching the angle of branching being commonly 30 degrees above the horizontal, the spread-to-height ratio being 1 to 2.

Lenticels: Average; small.

Leaves:

*Length.*—4¼ inches.

*Width.*—2 1/16 inches; medium size; outward pose; medium length/width ratio of blade; concave to straight shape in cross section; serrate indentation of margin; medium glossiness of upper side; medium pubescence on lower side; long petiole length; medium stipule size; medium time of bud burst; the color of the blade is R.H.S.C.C. 139C, the stems are R.H.S.C.C. 163C and 181B, and the veins are 160B.

Flower: Medium time of beginning of flowering (10% flowers); medium size; flat shape; margin of petals, touching; colour of bud just before flower opens, pink.

Fruit: Examined at peak maturity.

*Soluble solids.*—14.3.

*Size.*—Large; axial diameter 2 9/16 inches; transverse diameter 2 5/16 inches.

*Shape.*—Uniform; ellipsoid to ellipsoid conical; symmetrical in side view; ribbing absent; weak crowing at distal end.

*Cavity.*—Deep; medium width.

*Basin.*—Medium to deep depth; medium to broad width; ribbing, absent.

*Stem.*—Medium thickness (comparable to Cox's Orange Pippin); long length (comparable to Red Delicious).

*Calyx.*—Closed; Caylx tube length, long; calyx tube width; wide; caylx tube shape, Y shape.

*Sepal.*—Length, medium; spacing, free.

*Eye.*—Size, medium; apperture, open.

*Skin.*—Medium-thick; smooth; bloom of skin, absent; greasiness of skin, present; cracking tendency of skin, absent; background colour, yellow-green R.H.S.C.C. 14C.

*Over colour.*—Approximately sixty percent of over colour of skin (comparable to Gala); red R.H.S.C.C. 45B; striped; russet, absent.

*Flesh.*—Medium juiciness; firm; cream; crisp, melting; Penetrometer equals 8.2 kg. medium browning of flesh (one hour after being cut, with stainless steel knife).

*Texture.*—Medium.

*Flavour.*—Strong sweetness; weak acidity (pH about 4.3); sweet with low acid; less acid than Gala, less aromatic then Splendour.

*Weight of the fruit.*—180 gm.

*Quality.*—Excellent.

*Core.*—Distinctiveness of core line in cross section (median through locules), weak; apperture of locules in cross-section, open; central cavity (in cross section), absent.

*Sinus.*—Closed.

*Seeds.*—Five locules; 8 to 10 seeds total, 2 seeds per locule maximum; seed length 10 mm; seed width 5 mm; form obtuse; color R.H.S.C.C. 200A.

*Use.*—Market; dessert.

Keeping Quality: Very good; no disorders after 98 days.

Resistance to:

*Insects.*—Good.

*Diseases.*—Good.

Production: Early and regular cropping.

Growth habit: Standard, fruit bourne on short spurs.

Management: Trees require pruning in winter and fruit thinning in early summer. Trees in test plot trained as center leader trees. Natural habit is a conic open textured tree.

It is claimed:

1. A new and distinct variety of apple tree which is selected from seedlings derived from crossing the apple varieties Gala (U.S. Plant Pat. No. 3,637) and Splendour (U.S. Plant Pat. No. 2,460) substantially as shown and described characterised by its striped appearance and sweet flavour.

* * * * *